United States Patent
Alamro et al.

(10) Patent No.: US 12,365,588 B2
(45) Date of Patent: Jul. 22, 2025

(54) PRODUCTION OF SYNTHESIS GAS AND OF METHANOL

(71) Applicant: ENI S.P.A., Rome (IT)

(72) Inventors: Marwan Alamro, Thuwal (SA); Faisal Alahmadi, Thuwal (SA); Aspi Kolah, Thuwal (SA)

(73) Assignee: ENI S.p.A., Rome (IT)

( * ) Notice: Subject to any disclaimer, the term of this patent is extended or adjusted under 35 U.S.C. 154(b) by 806 days.

(21) Appl. No.: 17/436,938

(22) PCT Filed: Mar. 6, 2020

(86) PCT No.: PCT/IB2020/051988
§ 371 (c)(1),
(2) Date: Sep. 7, 2021

(87) PCT Pub. No.: WO2020/178802
PCT Pub. Date: Sep. 10, 2020

(65) Prior Publication Data
US 2022/0169502 A1 Jun. 2, 2022

Related U.S. Application Data (60) Provisional application No. 62/815,119, filed on Mar. 7, 2019.

(51) Int. Cl.
*C01B 3/38* (2006.01)
*C01B 3/48* (2006.01)
*C01B 3/50* (2006.01)

(52) U.S. Cl.
CPC ............... *C01B 3/386* (2013.01); *C01B 3/48* (2013.01); *C01B 3/50* (2013.01); *C01B 2203/0261* (2013.01); *C01B 2203/0283* (2013.01); *C01B 2203/061* (2013.01); *C01B 2203/0883* (2013.01); *C01B 2203/1241* (2013.01); *C01B 2203/148* (2013.01)

(58) Field of Classification Search
CPC .............. C01B 3/386; C01B 3/48; C01B 3/50
See application file for complete search history.

(56) References Cited

U.S. PATENT DOCUMENTS 9,394,219 B2 * 7/2016 Iaquaniello ......... C07C 29/1518
2018/0354877 A1 12/2018 Sakurai

FOREIGN PATENT DOCUMENTS

| EP | 0522744 A2 | 1/1993 | |
|----|---|---|---|
| WO | 2004083342 A1 | 9/2004 | |
| WO | WO-2012151605 A1 * | 11/2012 | ............... C01B 3/36 |
| WO | 2013062413 A1 | 5/2013 | |

OTHER PUBLICATIONS

International Search Report issued Jun. 12, 2020 re: Application No. PCT/IB2020/051988, pp. 1-5, citing: WO 2012/151605 A1, WO 2013/062413 A1, WO 2004/083342 A1, EP 0 522 744 A2, US 2018/0354877 A1.
Written Opinion issued Jun. 12, 2020 re: Application No. PCT/IB2020/051988, pp. 1-7, citing: WO 2012/151605 A1, WO 2013/062413 A1, WO 2004/083342 A1, EP 0 522 744 A2, US 2018/0354877 A1.
Chinese Office Action for Application No. 2020800317602, dated Dec. 19, 2024, 28 pages with translation.
Energy Conservation and Control, (US) F.G. Shinskey et al., Machinery Industry Press, p. 241, published on Sep. 30, 1987.
Gasification Process and Operation of Coal, compiled by Wuyun, Beijing Institute of Technology Press, 1st edition, 1st print in May 2013, p. 120.
Handbook of industrial Waste Disposal, (US) R.A. Conway et al., China Worker Press, p. 419, published on Oct. 31, 1983.
Introduction to Carbon-Chemical Engineering, Zhou Anning et al., China University of Mining and Technology Press, p. 28, published on Sep. 30, 2017.
Production Technology of Main Products of Carbon-Chemical Industry, compiled by Ying Weiyong et al., Chemical Industry Press, 1st edition, 1st printing in Mar. 2004, pp. 168-169.

* cited by examiner

Primary Examiner — Yong L Chu
(74) Attorney, Agent, or Firm — CANTOR COLBURN LLP (57) ABSTRACT

A system having a catalytic partial oxidation (CPO) reactor to produce, from a CPO reactant mixture, a CPO reactor effluent characterized by a hydrogen to carbon monoxide ($H_2/CO$) molar ratio and a M ratio defined as $(H_2-CO_2)/(CO+C=2)$. The system includes a water-gas shift (WGS) reactor configured to produce a hydrogen enriched reactor effluent from at least a portion of the CPO reactor effluent, wherein the hydrogen enriched reactor effluent is characterized by a $H_2/CO$ molar ratio that is greater than the $H_2/CO$ molar ratio of the CPO reactor effluent. The system includes a $CO_2$ separator operable to remove a portion of the $CO_2$ from the hydrogen enriched reactor effluent to yield the syngas, wherein the syngas is characterized by a M ratio that is greater than the M ratio of the CPO reactor effluent and of the hydrogen enriched reactor effluent. Processes for producing the syngas and producing methanol therefrom are also provided.

8 Claims, 1 Drawing Sheet

PRODUCTION OF SYNTHESIS GAS AND OF METHANOL

TECHNICAL FIELD

The present disclosure relates to systems and processes for producing synthesis gas via catalytic partial oxidation (CPO), and the production of methanol therefrom; more specifically, the present disclosure relates to systems and processes for producing methanol that employ water gas shift (WGS) and/or carbon dioxide ($CO_2$) separation downstream of CPO and upstream of methanol production; still more specifically, the present disclosure relates to systems and processes of producing methanol that provide a synthesis gas feed having a desired composition within the methanol synthesis loop via a combination of a CPO and WGS, $CO_2$ separation, and/or heat integration.

BACKGROUND

Synthesis gas (syngas) is a mixture comprising carbon monoxide (CO) and hydrogen ($H_2$), as well as small amounts of carbon dioxide ($CO_2$), water ($H_2O$), and unreacted methane ($CH_4$). Syngas is generally used as an intermediate in the production of methanol and ammonia, as well as an intermediate in creating synthetic petroleum to use as a lubricant or fuel.

Syngas is produced conventionally by steam reforming of natural gas (steam methane reforming or SMR), although other hydrocarbon sources can be used for syngas production, such as refinery off-gases, naphtha feedstocks, heavy hydrocarbons, coal, biomass, etc. SMR is an endothermic process and requires significant energy input to drive the reaction forward. Conventional endothermic technologies such as SMR produce syngas with a hydrogen content greater than the required content for methanol synthesis. Generally, SMR produces syngas with an M ratio ranging from 2.6 to 2.98, wherein the M ratio is a molar ratio defined as $(H_2-CO_2)/(CO+CO_2)$.

In an autothermal reforming (ATR) process, a portion of the natural gas is burned as fuel to drive the conversion of natural gas to syngas resulting in relatively low hydrogen and high $CO_2$ concentrations. Conventional methanol production plants utilize a combined reforming (CR) technology that pairs SMR with autothermal reforming (ATR) to reduce the amount of hydrogen present in syngas. ATR produces a syngas with a hydrogen content lower than that required for methanol synthesis. Generally, ATR produces syngas with an M ratio ranging from 1.7 to 1.84. In the CR technology, the natural gas feed volumetric flowrate to the SMR and the ATR can be adjusted to achieve an overall syngas M ratio of 2.0 to 2.06. Further, CR syngas has a hydrogen content greater than that required for methanol synthesis. Furthermore, SMR is a highly endothermic process, and the endothermicity of the SMR technology requires burning fuel to drive the syngas synthesis. Consequently, the SMR technology reduces the energy efficiency of the methanol synthesis process.

Syngas can also be produced (non-commercially) by catalytic partial oxidation (CPO or CPOx) of natural gas. CPO processes employ partial oxidation of hydrocarbon feeds to syngas comprising CO and $H_2$. The CPO process is exothermic, thus eliminating the need for external heat supply. However, the composition of the produced syngas is not directly suitable for a variety of downstream syntheses (e.g., methanol synthesis) owing to a reduced hydrogen content. Thus, there is an ongoing need for the development of systems and processes that utilize CPO processes for the production of synthesis gas suitable for downstream chemical synthesis (e.g., methanol synthesis).

BRIEF DESCRIPTION OF THE DRAWING

For a detailed description of the preferred embodiments of the disclosed processes, reference will now be made to the accompanying drawing in which.

DETAILED DESCRIPTION

Figure 1:
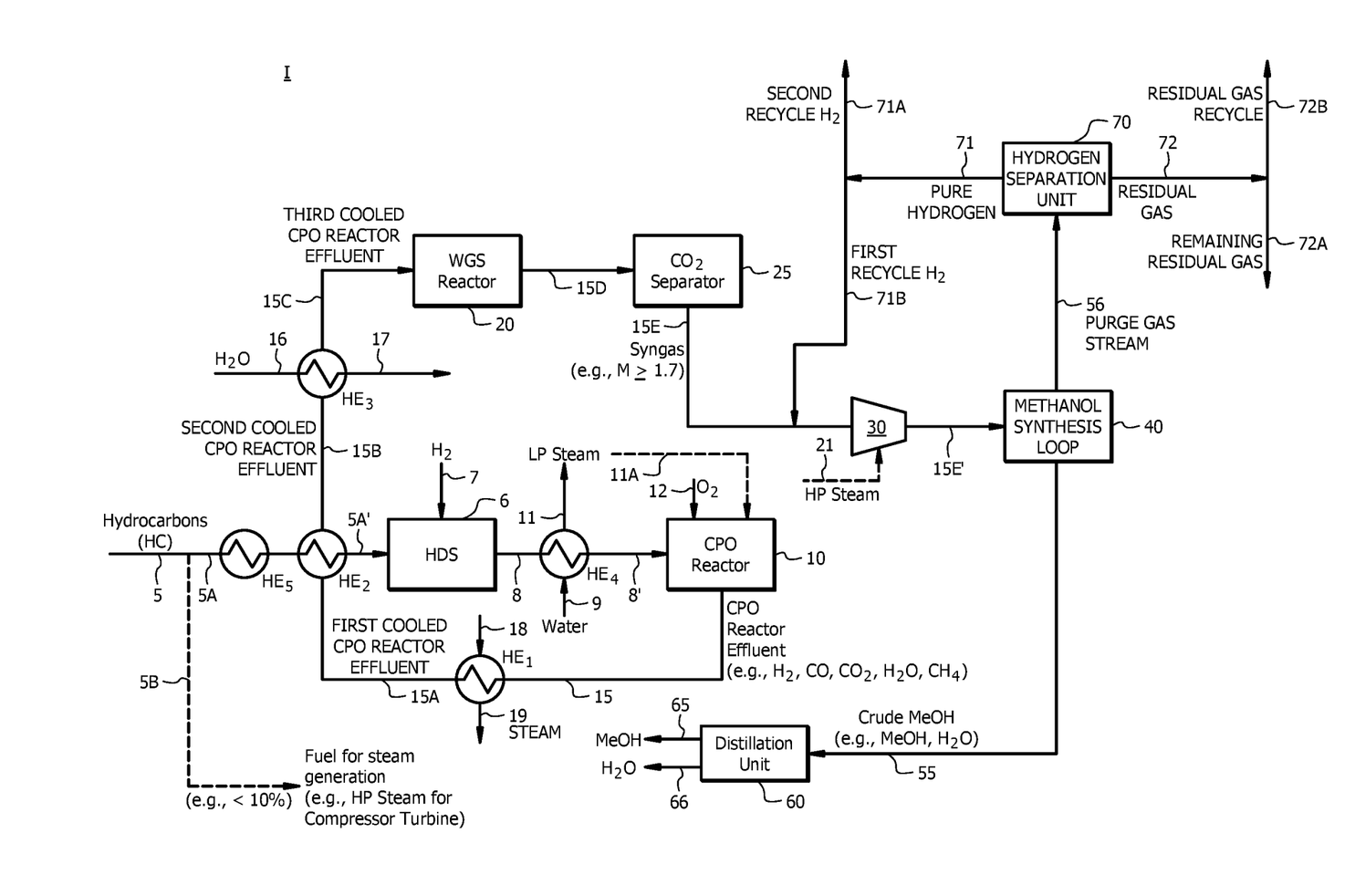
The FIGURE is a schematic of a system I for a synthesis gas and methanol synthesis process, according to embodiments of this disclosure.

Herein disclosed are a system and process for syngas production and optionally subsequent methanol synthesis therefrom using catalytic partial oxidation (CPO) of, for example, natural gas. The herein disclosed system and process adjust the composition of a CPO reactor effluent by using water gas shift (WGS) and carbon dioxide ($CO_2$) removal, and utilize heat integration for energy efficiency.

Conventional processes to produce syngas for methanol synthesis utilize standalone Steam Reforming (SMR) technology or combined reforming (CR) technology. Both of these conventional processes utilize endothermic steam reforming (SMR) to produce syngas with the required composition for methanol synthesis. The SMR reaction is a highly endothermic unit operation that is also high in capital expenses (CAPEX). Conventional best in class methanol plants utilize a combined reforming (CR) technology that consists of an SMR reactor and an Auto Thermal Reformer (ATR) to reduce the energy intensity of the syngas production, and thus of the overall methanol synthesis process. The CR process reduces the fuel consumption of the SMR unit by introducing an ATR to reform part of the natural gas feed. The natural gas feed (e.g., the volumetric flowrate) to the SMR and the ATR is adjusted to achieve an overall syngas composition (e.g., a syngas with an M value, as described further hereinbelow, of from about 2.0 to 2.06) produced by the CR technology.

The endothermicity of the SMR technology requires burning of a fuel to drive the reactions. Consequently, the SMR technology reduces the energy efficiency of a methanol synthesis process employing SMR to provide the synthesis gas feed to the methanol synthesis.

The herein disclosed system and process utilize a standalone CPO process in conjunction with WGS, $CO_2$ removal, and/or heat integration to produce a hydrogen enriched syngas with the required composition for downstream methanol synthesis without the need of an endothermic, and CAPEX intensive SMR. The herein disclosed methanol synthesis system and process are energy efficient and can be utilized, in embodiments, in a retrofit of an existing methanol production plant. By utilizing CPO, along with WGS, $CO_2$ removal, and/or heat integration, rather than SMR, the herein disclosed system and process allow for a reduced energy utilization with minimal capital expenditures.

In embodiments, the energy intensity of an existing methanol plant can be reduced according to this disclosure by retrofitting the existing plant. Alternatively, a new methanol plant having reduced energy intensity relative to a conventional methanol synthesis plant that utilizes SMR or CR can be designed according to this disclosure. The energy intensity is minimized according to this disclosure by integrating catalytic partial oxidation along with optional WGS, $CO_2$ removal, and/or process heat integration to produce similar or higher production rates of methanol with similar product quality. In embodiments, the energy intensity of a methanol synthesis plant (e.g., of a new or existing plant retrofitted as per this disclosure) is reduced from an indexed value of 100 to about 90, 80, or 70 MMBTU/ton of methanol produced In embodiments, the energy intensity of methanol production is reduced, via the system and process of this disclosure, by at least 10, 30, or 50% relative to conventional methanol production. In embodiments, the energy intensity of a methanol synthesis plant (e.g., of a new or existing plant retrofitted as per this disclosure) is reduced to an indexed value of less than or equal to about 40, 50, 60, 70, or 80 MMBTU/ton of methanol produced via the system and process of this disclosure.

Other than in the operating examples or where otherwise indicated, all numbers or expressions referring to quantities of ingredients, reaction conditions, and the like, used in the specification and claims are to be understood as modified in all instances by the term "about." Various numerical ranges are disclosed herein. Because these ranges are continuous, they include every value between the minimum and maximum values. The endpoints of all ranges reciting the same characteristic or component are independently combinable and inclusive of the recited endpoint. Unless expressly indicated otherwise, the various numerical ranges specified in this application are approximations. The endpoints of all ranges directed to the same component or property are inclusive of the endpoint and independently combinable. The term "from more than 0 to an amount" means that the named component is present in some amount more than 0, and up to and including the higher named amount.

The terms "a," "an," and "the" do not denote a limitation of quantity, but rather denote the presence of at least one of the referenced item. As used herein the singular forms "a," "an," and "the" include plural referents.

As used herein, "combinations thereof" is inclusive of one or more of the recited elements, optionally together with a like element not recited, e.g., inclusive of a combination of one or more of the named components, optionally with one or more other components not specifically named that have essentially the same function. As used herein, the term "combination" is inclusive of blends, mixtures, alloys, reaction products, and the like.

Reference throughout the specification to "an embodiment," "another embodiment," "other embodiments," "some embodiments," and so forth, means that a particular element (e.g., feature, structure, property, and/or characteristic) described in connection with the embodiment is included in at least an embodiment described herein, and may or may not be present in other embodiments. In addition, it is to be understood that the described element(s) can be combined in any suitable manner in the various embodiments.

As used herein, the terms "inhibiting" or "reducing" or "preventing" or "avoiding" or any variation of these terms, include any measurable decrease or complete inhibition to achieve a desired result.

As used herein, the term "effective," means adequate to accomplish a desired, expected, or intended result.

As used herein, the terms "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains") are inclusive or open-ended and do not exclude additional, unrecited elements or process steps.

Unless defined otherwise, technical and scientific terms used herein have the same meaning as is commonly understood by one of skill in the art.

Compounds are described herein using standard nomenclature. For example, any position not substituted by any indicated group is understood to have its valency filled by a bond as indicated, or a hydrogen atom. A dash ("-") that is not between two letters or symbols is used to indicate a point of attachment for a substituent. For example, —CHO is attached through the carbon of the carbonyl group.

As used herein, the terms "$C_x$ hydrocarbons" and "$C_x$s" are interchangeable and refer to any hydrocarbon having x number of carbon atoms (C). For example, the terms "$C_4$ hydrocarbons" and "$C_4$s" both refer to any hydrocarbons having exactly 4 carbon atoms, such as n-butane, iso-butane, cyclobutane, 1-butene, 2-butene, isobutylene, butadiene, and the like, or combinations thereof.

As used herein, the term "$C_{x+}$ hydrocarbons" refers to any hydrocarbon having greater than or equal to x carbon atoms (C). For example, the term "$C_{2+}$ hydrocarbons" refers to any hydrocarbons having 2 or more carbon atoms, such as ethane, ethylene, $C_3$s, $C_4$s, $C_5$s, etc.

As utilized herein, the 'methanol synthesis loop' or 'methanol loop' refers to the methanol synthesis section of a plant, comprising the methanol synthesis reactor(s).

As utilized herein, the M ratio is a molar ratio defined as $(H_2-CO_2)/(CO+CO_2)$.

Referring to The FIGURE, a syngas and methanol production system I is disclosed. The syngas and methanol production system I generally comprises a catalytic partial oxidation (CPO or CPOx) reactor 10; a water gas shift (WGS) reactor 20, a carbon dioxide ($CO_2$) separator 25; a compressor 30; and a methanol synthesis loop 40. In embodiments, the syngas and methanol synthesis system I can further comprise a desulfurization unit 6, a hydrogen separation unit 70, a distillation unit 60, and one or more heat exchangers, such as first heat exchanger HE1, second heat exchanger HE2, third heat exchanger HE3, fourth heat exchanger HE4, and/or fifth heat exchanger (e.g., an electric heater) HE5. As will be appreciated by one of skill in the art, and with the help of this disclosure, syngas and methanol production system components shown in The FIGURE can be in fluid communication with each other (as represented by the connecting lines indicating a direction of fluid flow) through any suitable conduits (e.g., pipes, streams, etc.).

In embodiments, a process as disclosed herein can comprise a step of (a) reacting, via a catalytic partial oxidation (CPO) reaction, a CPO reactant mixture in a CPO reactor 10 to produce a CPO reactor effluent 15 comprising syngas; wherein the CPO reactant mixture comprises hydrocarbons, oxygen, and optionally water; wherein the CPO reactor 10 comprises a CPO catalyst; wherein the CPO reactor effluent 15 comprises hydrogen ($H_2$), carbon monoxide (CO), carbon dioxide ($CO_2$), water, and unreacted hydrocarbons, wherein the CPO reactor effluent 15 is characterized by a hydrogen to carbon monoxide ($H_2$/CO) molar ratio of the CPO reactor effluent, and wherein the CPO reactor effluent 15 is characterized by an M ratio of the CPO reactor effluent, wherein the M ratio is a molar ratio defined as $(H_2-CO_2)/(CO+CO_2)$. As described further hereinbelow, the CPO reactant mixture can comprise a combination oxygen in line 12, steam in line 11A, and a first hydrocarbon portion 5A of a hydrocarbon feed 5 optionally heat exchanged in second heat exchanger HE2 to produce heat exchanged first portion 5A', desulfurized in desulfurization unit 6 to provide desulfurized first portion in line 8, and/or heat exchanged in fourth heat exchanger HE4 to provide heat exchanged desulfurized first portion 8'.

Generally, the CPO reaction is based on partial combustion of fuels, such as various hydrocarbons, and in the case of methane, CPO can be represented by Equation (1):

$$CH_4 + \tfrac{1}{2}O_2 \rightarrow CO + 2H_2 \quad (1)$$

Without wishing to be limited by theory, side reactions can take place along with the CPO reaction depicted in Equation (1); and such side reactions can produce carbon dioxide ($CO_2$) and water ($H_2O$), for example via hydrocarbon combustion, which is an exothermic reaction. As will be appreciated by one of skill in the art, and with the help of this disclosure, and without wishing to be limited by theory, the CPO reaction as represented by Equation (1) can yield a syngas with a hydrogen to carbon monoxide ($H_2/CO$) molar ratio having the theoretical stoichiometric limit of 2.0. Without wishing to be limited by theory, the theoretical stoichiometric limit of 2.0 for the $H_2/CO$ molar ratio means that the CPO reaction as represented by Equation (1) yields 2 moles of $H_2$ for every 1 mole of CO, i.e., $H_2/CO$ molar ratio of (2 moles $H_2$/1 mole CO)=2. As will be appreciated by one of skill in the art, and with the help of this disclosure, the theoretical stoichiometric limit of 2.0 for the $H_2/CO$ molar ratio in a CPO reaction cannot be achieved practically because reactants (e.g., hydrocarbons, oxygen) as well as products (e.g., $H_2$, CO) undergo side reactions at the conditions used for the CPO reaction. As will be appreciated by one of skill in the art, and with the help of this disclosure, and without wishing to be limited by theory, in the presence of oxygen, CO and $H_2$ can be oxidized to $CO_2$ and $H_2O$, respectively. The relative amounts (e.g., composition) of CO, $H_2$, $CO_2$ and $H_2O$ can be further altered by the equilibrium of the water-gas shift (WGS) reaction, which will be discussed in more detail later herein. The side reactions that can take place in the CPO reactor 10 can have a direct impact on the M ratio of the produced syngas (e.g., the syngas in CPO reactor effluent 15), wherein the M ratio is a molar ratio defined as $(H_2-CO_2)/(CO+CO_2)$. In the absence of any side reaction (theoretically), the CPO reaction as represented by Equation (1) results in a syngas with an M ratio of 2.0. However, the presence of side reactions (practically) reduces $H_2$ and increases $CO_2$, thereby resulting in a syngas in the CPO reactor effluent 15 with an M ratio below 2.0.

Further, without wishing to be limited by theory, the CPO reaction as depicted in Equation (1) is an exothermic heterogeneous catalytic reaction (i.e., a mildly exothermic reaction) and it occurs in a single reactor unit, such as the CPO reactor 10 (as opposed to more than one reactor unit as is the case in conventional processes for syngas production, such as steam methane reforming (SMR)—autothermal reforming (ATR) combinations). While it is possible to conduct partial oxidation of hydrocarbons as a homogeneous reaction, in the absence of a catalyst, homogeneous partial oxidation of hydrocarbons process entails excessive temperatures, long residence times, as well as excessive coke formation, which strongly reduce the controllability of the partial oxidation reaction, and may not produce syngas of the desired quality in a single reactor unit.

Furthermore, without wishing to be limited by theory, the CPO reaction is fairly resistant to chemical poisoning, and as such it allows for the use of a wide variety of hydrocarbon feedstocks, including some sulfur containing hydrocarbon feedstocks; which, in some cases, can enhance catalyst life-time and productivity. By contrast, conventional ATR processes have more restrictive feed requirements, for example in terms of content of impurities in the feed (e.g., feed to ATR is desulfurized), as well as hydrocarbon composition (e.g., ATR primarily uses a $CH_4$-rich feed).

In embodiments, the hydrocarbons (e.g., in hydrocarbon feed 5) suitable for use in a CPO reaction as disclosed herein can include methane ($CH_4$), natural gas, natural gas liquids, liquefied petroleum gas (LPG), associated gas, well head gas, enriched gas, paraffins, shale gas, shale liquids, fluid catalytic cracking (FCC) off gas, refinery process gases, refinery off gases, stack gases, fuel gas from a fuel gas header, and the like, or combinations thereof. The hydrocarbons can include any suitable hydrocarbons source, and can contain $C_1$-$C_6$ hydrocarbons, as well some heavier hydrocarbons.

In embodiments, the CPO reactant mixture in CPO reactor 10 can comprise hydrocarbons from hydrocarbon feed 5, which can comprise, consist essentially of, or consist of natural gas. A first portion 5A of the hydrocarbon feed 5 can be utilized as process gas (e.g., process natural gas PNG)), and directed toward CPO reactor 10, while a second portion 5B of the hydrocarbon feed 5 can be utilized as fuel gas (e.g., fuel natural gas (FNG)), and directed elsewhere throughout system I for use as a fuel (e.g., for steam generation, such as for the production of high pressure (HP) steam to run a turbine, e.g. to run a turbine of compressor 30). In embodiments, the second portion 5B of hydrocarbons utilized as fuel comprise less than about 10, 9, 8, 7, 6, 5, 4, 3, 2, or 1 wt % of the total hydrocarbon feed 5, based on the total weight of the total hydrocarbons, wherein the total hydrocarbons are given by the sum of the hydrocarbons introduced to the CPO reactor in step (a) via first portion 5A and the hydrocarbons directed as fuel via the second portion 5B.

Generally, natural gas is composed primarily of methane, but can also contain ethane, propane and heavier hydrocarbons (e.g., iso-butane, n-butane, iso-pentane, n-pentane, hexanes, etc.), as well as very small quantities of nitrogen, oxygen, carbon dioxide, sulfur compounds, and/or water. The natural gas can be provided from a variety of sources including, but not limited to, gas fields, oil fields, coal fields, fracking of shale fields, biomass, landfill gas, and the like, or combinations thereof. In some embodiments, the CPO reactant mixture can comprise $CH_4$ and $C_2$.

The natural gas can comprise any suitable amount of methane. In some embodiments, the natural gas can comprise biogas. For example, the natural gas can comprise from about 45 mol % to about 80 mol % methane, from about 20 mol % to about 55 mol % carbon dioxide, and less than about 15 mol % nitrogen.

In embodiments, natural gas (or the hydrocarbon feed 5) can comprise $CH_4$ in an amount of greater than or equal to about 45 mol %, alternatively greater than or equal to about 50 mol %, alternatively greater than or equal to about 55 mol %, alternatively greater than or equal to about 60 mol %, alternatively greater than or equal to about 65 mol %, alternatively greater than or equal to about 70 mol %, alternatively greater than or equal to about 75 mol %, alternatively greater than or equal to about 80 mol %, alternatively greater than or equal to about 82 mol %, alternatively greater than or equal to about 84 mol %, alternatively greater than or equal to about 86 mol %, alternatively greater than or equal to about 88 mol %, alternatively greater than or equal to about 90 mol %, alternatively greater than or equal to about 91 mol %, alternatively greater than or equal to about 92 mol %, alternatively greater than or equal to about 93 mol %, alternatively greater than or equal to about 94 mol %, alternatively greater than or equal to about 95 mol %, alternatively greater than or equal to about 96 mol %, alternatively greater than or equal to about 97 mol %, alternatively greater than or equal to about 98 mol %, or alternatively greater than or equal to about 99 mol %.

In some embodiments, the hydrocarbons in hydrocarbon feed 5 suitable for use in a CPO reaction as disclosed herein can comprise $C_1$-$C_6$ hydrocarbons, nitrogen (e.g., from about 0.1 mol % to about 15 mol %, alternatively from about 0.5 mol % to about 11 mol %, alternatively from about 1 mol % to about 7.5 mol %, or alternatively from about 1.3 mol % to about 5.5 mol %), and carbon dioxide (e.g., from about 0.1 mol % to about 2 mol %, alternatively from about 0.2 mol % to about 1 mol %, or alternatively from about 0.3 mol % to about 0.6 mol %). For example, the hydrocarbons suitable for use in a CPO reaction as disclosed herein can comprise $C_1$ hydrocarbon (about 89 mol % to about 92 mol %); $C_2$ hydrocarbons (about 2.5 mol % to about 4 mol %); $C_3$ hydrocarbons (about 0.5 mol % to about 1.4 mol %); $C_4$ hydrocarbons (about 0.5 mol % to about 0.2 mol %); $C_5$ hydrocarbons (about 0.06 mol %); and $C_6$ hydrocarbons (about 0.02 mol %); and optionally nitrogen (about 0.1 mol % to about 15 mol %), carbon dioxide (about 0.1 mol % to about 2 mol %), or both nitrogen (about 0.1 mol % to about 15 mol %) and carbon dioxide (about 0.1 mol % to about 2 mol %). Accordingly, the CPO reactant mixture can comprise such hydrocarbons, which can be introduced into CPO reactor 10 via first portion 5A of hydrocarbon feed 5, or separately.

The oxygen used in the CPO reactant mixture 10 can comprise 100% oxygen (substantially pure $O_2$), oxygen gas (which may be obtained via a membrane separation process), technical oxygen (which may contain some air), air, oxygen enriched air, oxygen-containing gaseous compounds (e.g., NO), oxygen-containing mixtures (e.g., $O_2/CO_2$, $O_2/H_2O$, $O_2/H_2O_2/H_2O$), oxy radical generators (e.g., $CH_3OH$, $CH_2O$), hydroxyl radical generators, and the like, or combinations thereof. Oxygen can be introduced into CPO reactor 10 via oxygen line 12, in embodiments, or elsewhere (e.g., along with desulfurized first portion 8 or heat exchanged desulfurized first portion 8').

In embodiments, the CPO reactant mixture in CPO reactor 10 can be characterized by a carbon to oxygen (C/O) molar ratio of less than or equal to about 3:1, alternatively less than or equal to about 2.6:1, alternatively less than or equal to about 2.4:1, alternatively less than or equal to about 2.2:1, alternatively less than or equal to about 2:1, alternatively less than or equal to about 1.9:1, alternatively less than or equal to about 1.8:1, alternatively less than or equal to about 1.75:1, alternatively greater than or equal to about 2:1, alternatively greater than or equal to about 2.2:1, alternatively greater than or equal to about 2.4:1, alternatively greater than or equal to about 2.6:1, alternatively from about 0.5:1 to about 3:1, alternatively from about 0.7:1 to about 2.5:1, alternatively from about 0.9:1 to about 2.2:1, alternatively from about 1:1 to about 2:1, alternatively from about 1.1:1 to about 1.9:1, alternatively from about 1.5:1 to about 2.5:1, alternatively from about 1.6:1 to about 2.5:1, alternatively from about 2:1 to about 3:1, alternatively from about 2.2:1 to about 3:1, alternatively from about 2.4:1 to about 3:1, or alternatively from about 2.6:1 to about 3:1, wherein the C/O molar ratio refers to the total moles of carbon (C) of hydrocarbons in the reactant mixture divided by the total moles of oxygen ($O_2$) in the reactant mixture.

For example, when the only source of carbon in the CPO reactant mixture in CPO reactor 10 is $CH_4$ (e.g., introduced via first portion 5A of hydrocarbon stream 5), the $CH_4/O_2$ molar ratio is the same as the C/O molar ratio. As another example, when the CPO reactant mixture contains other carbon sources besides $CH_4$, such as ethane ($C_2H_6$), propane ($C_3H_3$), butanes ($C_4H_{10}$), etc., the C/O molar ratio accounts for the moles of carbon in each compound (e.g., 2 moles of C in 1 mole of $C_2H_6$, 3 moles of C in 1 mole of $C_3H_3$, 4 moles of C in 1 mole of $C_4H_{10}$, etc.). As will be appreciated by one of skill in the art, and with the help of this disclosure, the C/O molar ratio in the CPO reactant mixture can be adjusted along with other reactor process parameters (e.g., temperature, pressure, flow velocity, etc.) to provide for a syngas with a desired composition (e.g., a syngas with a desired $H_2/CO$ molar ratio; a syngas with a desired $CO_2$ content; etc.). The C/O molar ratio in the CPO reactant mixture can be adjusted to provide for a decreased amount of unconverted hydrocarbons in the syngas. The C/O molar ratio in the CPO reactant mixture can be adjusted based on the CPO effluent temperature in order to decrease (e.g., minimize) the unconverted hydrocarbons content of the syngas in CPO reactor effluent 15. As will be appreciated by one of skill in the art, and with the help of this disclosure, when the syngas is further used in a methanol production process, unconverted hydrocarbons present in the syngas can undesirably accumulate in a methanol reaction loop, thereby decreasing the efficiency of the methanol production process.

In embodiments, the hydrocarbon feed 5 further comprise one or more sulfur-containing compounds, and at least a portion of the sulfur-containing compounds is removed from the first portion 5A of the hydrocarbon feed 5 prior to introducing the hydrocarbons to the CPO reactor 10 as a component of the CPO reactant mixture. In such embodiments, the first portion 5A (optionally following heat exchange thereto from CPO reactor effluent 15 to provide heat exchanged first portion of hydrocarbons 5A', which is described further hereinbelow) of hydrocarbon feed 5 can be introduced into a desulfurization unit 6 for the removal of one or more sulfur-containing compounds therefrom. Any suitable desulfurization unit 6 known to those of skill in the art can be utilized. For example, in embodiments, desulfurization unit 6 comprises a hydrodesulfurization (HDS) unit 6, and hydrogen is introduced into the desulfurization unit 6 via hydrogen line 7. A desulfurized first portion of hydrocarbons 8 can be removed from desulfurization unit 6. The desulfurized first portion of hydrocarbons 8 can be introduced into CPO reactor 10 (optionally following heat exchange therefrom to provide heat exchanged desulfurized first portion of hydrocarbons 8', which is described further hereinbelow).

In embodiments, a CPO reactor 10 suitable for use in the present disclosure can comprise a tubular reactor, a continuous flow reactor, a fixed bed reactor, a fluidized bed reactor, a moving bed reactor, a circulating fluidized bed reactor (e.g., a riser type reactor), a bubbling bed reactor, an ebullated bed reactor, a rotary kiln reactor, and the like, or combinations thereof. In some embodiments, the CPO reactor 10 can comprise a circulating fluidized bed reactor, such as a riser type reactor.

In some embodiments, the CPO reactor 10 can be characterized by at least one CPO operational parameter selected from the group consisting of a CPO reactor temperature (e.g., CPO catalyst bed temperature); CPO feed temperature (e.g., CPO reactant mixture temperature); target CPO effluent temperature; a CPO pressure (e.g., CPO reactor pressure); a CPO contact time (e.g., CPO reactor contact time); a C/O molar ratio in the CPO reactant mixture; a steam to carbon (S/C) molar ratio in the CPO reactant mixture, wherein the S/C molar ratio refers to the total moles of water (H₂O) in the reactant mixture divided by the total moles of carbon (C) of hydrocarbons in the reactant mixture; and combinations thereof. For purposes of the disclosure herein, the CPO effluent temperature is the temperature of the syngas (e.g., syngas effluent; CPO reactor effluent 15) measured at the point where the syngas exits the CPO reactor (CPO reactor 10), e.g., a temperature of the syngas measured at a CPO reactor outlet, a temperature of the syngas effluent, a temperature of the exit syngas effluent. For purposes of the disclosure herein, the CPO effluent temperature (e.g., target CPO effluent temperature) is considered an operational parameter. As will be appreciated by one of skill in the art, and with the help of this disclosure, the choice of operational parameters for the CPO reactor such as CPO feed temperature; CPO pressure; CPO contact time; C/O molar ratio in the CPO reactant mixture; S/C molar ratio in the CPO reactant mixture; etc. determines the temperature of the syngas effluent (e.g., CPO reactor effluent 15), as well as the composition of the syngas effluent (e.g., syngas in CPO reactor effluent 15). Further, and as will be appreciated by one of skill in the art, and with the help of this disclosure, monitoring the CPO effluent temperature can provide feedback for changing other operational parameters (e.g., CPO feed temperature; CPO pressure; CPO contact time; C/O molar ratio in the CPO reactant mixture; S/C molar ratio in the CPO reactant mixture; etc.) as necessary for the CPO effluent temperature to match the target CPO effluent temperature. Furthermore, and as will be appreciated by one of skill in the art, and with the help of this disclosure, the target CPO effluent temperature is the desired CPO effluent temperature, and the CPO effluent temperature (e.g., measured CPO effluent temperature, actual CPO effluent temperature) may or may not coincide with the target CPO effluent temperature. In embodiments where the CPO effluent temperature is different from the target CPO effluent temperature, one or more CPO operational parameters (e.g., CPO feed temperature; CPO pressure; CPO contact time; C/O molar ratio in the CPO reactant mixture; S/C molar ratio in the CPO reactant mixture; etc.) can be adjusted (e.g., modified) in order for the CPO effluent temperature to match (e.g., be the same with, coincide with) the target CPO effluent temperature. The CPO reactor 10 can be operated under any suitable operational parameters that can provide for a syngas with a desired composition (e.g., a syngas with a desired H₂/CO molar ratio; a syngas with a desired CO₂ content; etc.).

The CPO reactor 10 can be characterized by a CPO feed temperature of from about 25° C. to about 600° C., alternatively from about 25° C. to about 500° C., alternatively from about 25° C. to about 400° C., alternatively from about 50° C. to about 400° C., alternatively from about 100° C. to about 400° C., or alternatively less than or equal to about 600, 500, or 400° C.

The CPO reactor 10 can be characterized by a CPO effluent temperature (e.g., target temperature of CPO reactor effluent 15) of greater than or equal to about 300° C., greater than or equal to about 600° C., alternatively greater than or equal to about 700° C., alternatively greater than or equal to about 750° C., alternatively greater than or equal to about 800° C., alternatively greater than or equal to about 850° C., alternatively from about 300° C. to about 1,600° C., alternatively from about 600° C. to about 1,400° C., alternatively from about 600° C. to about 1,300° C., alternatively from about 700° C. to about 1,200° C., alternatively from about 750° C. to about 1,150° C., alternatively from about 800° C. to about 1,125° C., or alternatively from about 850° C. to about 1,100° C.

In embodiments, the CPO reactor 10 can be characterized by any suitable reactor temperature and/or catalyst bed temperature. For example, the CPO reactor 10 can be characterized by a reactor temperature and/or catalyst bed temperature of greater than or equal to about 300° C., alternatively greater than or equal to about 600° C., alternatively greater than or equal to about 700° C., alternatively greater than or equal to about 750° C., alternatively greater than or equal to about 800° C., alternatively greater than or equal to about 850° C., alternatively from about 300° C. to about 1,600° C., alternatively from about 600° C. to about 1,400° C., alternatively from about 600° C. to about 1,300° C., alternatively from about 700° C. to about 1,200° C., alternatively from about 750° C. to about 1,150° C., alternatively from about 800° C. to about 1,125° C., or alternatively from about 850° C. to about 1,100° C.

The CPO reactor 10 can be operated under any suitable temperature profile that can provide for a syngas with a desired composition (e.g., a syngas with a desired H₂/CO molar ratio; a syngas with a desired CO₂ content; etc.). The CPO reactor 10 can be operated under adiabatic conditions, non-adiabatic conditions, isothermal conditions, near-isothermal conditions, etc. For purposes of the disclosure herein, the term "non-adiabatic conditions" refers to process conditions wherein a reactor is subjected to external heat exchange or transfer (e.g., the reactor is heated; or the reactor is cooled), which can be direct heat exchange and/or indirect heat exchange. As will be appreciated by one of skill in the art, and with the help of this disclosure, the terms "direct heat exchange" and "indirect heat exchange" are known to one of skill in the art. By contrast, the term "adiabatic conditions" refers to process conditions wherein a reactor is not subjected to external heat exchange (e.g., the reactor is not heated; or the reactor is not cooled). Generally, external heat exchange implies an external heat exchange system (e.g., a cooling system; a heating system) that requires energy input and/or output. External heat transfer can also result from heat loss from the catalyst bed (or reactor) due to radiation, conduction or convection. For example, this heat exchange from the catalyst bed can be to the external environment or to the reactor zones before and after the catalyst bed.

For purposes of the disclosure herein, the term "isothermal conditions" refers to process conditions (e.g., CPO operational parameters) that allow for a substantially constant temperature of the reactor and/or catalyst bed (e.g., isothermal temperature) that can be defined as a temperature that varies by less than about ±10° C., alternatively less than about ±9° C., alternatively less than about ±8° C., alternatively less than about ±7° C., alternatively less than about ±6° C., alternatively less than about ±5° C., alternatively less than about ±4° C., alternatively less than about ±3° C., alternatively less than about ±2° C., or alternatively less than about ±1° C. across the reactor and/or catalyst bed, respectively.

Further, for purposes of the disclosure herein, the term "isothermal conditions" refers to process conditions (e.g., CPO operational parameters) effective for providing for a syngas with a desired composition (e.g., a desired H₂/CO molar ratio; a desired CO₂ content; etc.), wherein the isothermal conditions comprise a temperature variation of less than about +10° C. across the reactor and/or catalyst bed. In embodiments, CPO reactor 10 can be operated under any suitable operational parameters that can provide for isothermal conditions.

For purposes of the disclosure herein, the term "near-isothermal conditions" refers to process conditions (e.g., CPO operational parameters) that allow for a fairly constant temperature of the reactor and/or catalyst bed (e.g., near-isothermal temperature), which can be defined as a temperature that varies by less than about ±100° C., alternatively less than about ±90° C., alternatively less than about ±80° C., alternatively less than about ±70° C., alternatively less than about ±60° C., alternatively less than about ±50° C., alternatively less than about ±40° C., alternatively less than about ±30° C., alternatively less than about ±20° C., alternatively less than about ±10° C., alternatively less than about ±9° C., alternatively less than about ±8° C., alternatively less than about ±7° C., alternatively less than about +6° C., alternatively less than about ±5° C., alternatively less than about ±4° C., alternatively less than about +3° C., alternatively less than about ±2° C., or alternatively less than about ±1° C. across the reactor and/or catalyst bed, respectively. In some embodiments, near-isothermal conditions allow for a temperature variation of less than about ±50° C., alternatively less than about ±25° C., or alternatively less than about ±10° C. across the reactor and/or catalyst bed. Further, for purposes of the disclosure herein, the term "near-isothermal conditions" is understood to include "isothermal" conditions.

Furthermore, for purposes of the disclosure herein, the term "near-isothermal conditions" refers to process conditions (e.g., CPO operational parameters) effective for providing for a syngas with a desired composition (e.g., a desired $H_2/CO$ molar ratio; a desired $CO_2$ content; etc.), wherein the near-isothermal conditions comprise a temperature variation of less than about ±100° C. across the reactor and/or catalyst bed.

In embodiments, a process as disclosed herein can comprise conducting the CPO reaction under near-isothermal conditions to produce syngas, wherein the near-isothermal conditions comprise a temperature variation of less than about ±100° C. across the reactor and/or catalyst bed. In embodiments, the CPO reactor 10 can be operated under any suitable operational parameters that can provide for near-isothermal conditions.

Near-isothermal conditions can be provided by a variety of process and catalyst variables, such as temperature (e.g., heat exchange or heat transfer), pressure, gas flow rates, reactor configuration, catalyst bed configuration, catalyst bed composition, reactor cross sectional area, feed gas staging, feed gas injection, feed gas composition, and the like, or combinations thereof. Generally, and without wishing to be limited by theory, the terms "heat transfer" or "heat exchange" refer to thermal energy being exchanged or transferred between two systems (e.g., two reactors, such as a CPO reactor and a cracking reactor), and the terms "heat transfer" or "heat exchange" are used interchangeably for purposes of the disclosure herein.

In some embodiments, achieving a target CPO effluent temperature and/or near-isothermal conditions can be provided by heat exchange or heat transfer. The heat exchange can comprise heating the reactor; or cooling the reactor. In embodiments, achieving a target CPO effluent temperature and/or near-isothermal conditions can be provided by cooling the reactor. In another embodiment, achieving a target CPO effluent temperature and/or near-isothermal conditions can be provided by heating the reactor.

In some embodiments, achieving a target CPO effluent temperature and/or near-isothermal conditions can be provided by direct heat exchange and/or indirect heat exchange. As will be appreciated by one of skill in the art, and with the help of this disclosure, the terms "direct heat exchange" and "indirect heat exchange" are known to one of skill in the art.

The heat exchange can comprise external heat exchange, external coolant fluid cooling, reactive cooling, liquid nitrogen cooling, cryogenic cooling, electric heating, electric arc heating, microwave heating, radiant heating, natural gas combustion, solar heating, infrared heating, use of a diluent in the CPO reactant mixture, and the like, or combinations thereof. For example, reactive cooling can be effected by carrying out an endothermic reaction in a cooling coil/jacket associated with (e.g., located in) the reactor.

In some embodiments, achieving a target CPO effluent temperature and/or near-isothermal conditions can be provided by removal of process heat from the CPO reactor. In other embodiments, achieving a target CPO effluent temperature and/or near-isothermal conditions can be provided by supplying heat to the CPO reactor. As will be appreciated by one of skill in the art, and with the help of this disclosure, a CPO reactor may need to undergo both heating and cooling in order to achieve a target CPO effluent temperature and/or near-isothermal conditions.

In embodiments, the heat exchange or heat transfer can comprise introducing a cooling agent, such as a diluent, into the reactor (e.g., CPO reactor 10), to decrease the reactor temperature and/or the catalyst bed temperature, while increasing a temperature of the cooling agent and/or changing the phase of the cooling agent. The cooling agent can be reactive or non-reactive. The cooling agent can be in liquid state and/or in vapor state. As will be appreciated by one of skill in the art, and with the help of this disclosure, the cooling agent can act as a flammability retardant; for example by reducing the temperature inside the reactor, by changing the gas mixture composition, by reducing the combustion of hydrocarbons to carbon dioxide; etc.

In some embodiments, the CPO reactant mixture in CPO reactor 10 can further comprise a diluent, wherein the diluent contributes to achieving a target CPO effluent temperature and/or near-isothermal conditions via heat exchange, as disclosed herein. The diluent can comprise water, steam, inert gases (e.g., argon), nitrogen, carbon dioxide, and the like, or combinations thereof. Generally, the diluent is inert with respect to the CPO reaction, e.g., the diluent does not participate in the CPO reaction. However, and as will be appreciated by one of skill in the art, and with the help of this disclosure, some diluents (e.g., water, steam, carbon dioxide, etc.) might undergo chemical reactions other than the CPO reaction within the reactor, and can change the composition of the resulting syngas, as will be described in more detail later herein; while other diluents (e.g., nitrogen ($N_2$), argon (Ar)) might not participate in reactions that change the composition of the resulting syngas. As will be appreciated by one of skill in the art, and with the help of this disclosure, the diluent can be used to vary the composition of the resulting syngas (e.g., the syngas in CPO reactor effluent 15). The diluent can be present in the CPO reactant mixture in any suitable amount.

The CPO reactor 10 can be characterized by a CPO pressure (e.g., reactor pressure measured at the CPO reactor exit or outlet) of greater than or equal to about 1 barg, alternatively greater than or equal to about 10 barg, alternatively greater than or equal to about 20 barg, alternatively greater than or equal to about 25 barg, alternatively greater than or equal to about 30 barg, alternatively greater than or equal to about 35 barg, alternatively greater than or equal to about 40 barg, alternatively greater than or equal to about 50 barg, alternatively less than about 30 barg, alternatively less than about 25 barg, alternatively less than about 20 barg, alternatively less than about 10 barg, alternatively from about 1 barg to about 90 barg, alternatively from about 1 barg to about 70 barg, alternatively from about 1 barg to about 40 barg, alternatively from about 1 barg to about 30 barg, alternatively from about 1 barg to about 25 barg, alternatively from about 1 barg to about 20 barg, alternatively from about 1 barg to about 10 barg, alternatively from about 20 barg to about 90 barg, alternatively from about 25 barg to about 85 barg, or alternatively from about 30 barg to about 80 barg.

The CPO reactor 10 can be characterized by a CPO contact time of from about 0.001 milliseconds (ms) to about 5 seconds (s), alternatively from about 0.001 ms to about 1 s, alternatively from about 0.001 ms to about 100 ms, alternatively from about 0.001 ms to about 10 ms, alternatively from about 0.001 ms to about 5 ms, or alternatively from about 0.01 ms to about 1.2 ms. Generally, the contact time of a reactor comprising a catalyst refers to the average amount of time that a compound (e.g., a molecule of that compound) spends in contact with the catalyst (e.g., within the catalyst bed), e.g., the average amount of time that it takes for a compound (e.g., a molecule of that compound) to travel through the catalyst bed. In some embodiments, the CPO reactor 10 can be characterized by a contact time of from about 0.001 ms to about 5 ms, or alternatively from about 0.01 ms to about 1.2 ms.

All of the CPO operational parameters disclosed herein are applicable throughout all of the embodiments disclosed herein, unless otherwise specified. As will be appreciated by one of skill in the art, and with the help of this disclosure, each CPO operational parameter can be adjusted to provide for a desired syngas quality (e.g., of CPO reactor effluent 15), such as a syngas with a desired composition (e.g., a syngas with a desired $H_2/CO$ molar ratio; a syngas with a desired $CO_2$ content; etc.). For example, the CPO operational parameters can be adjusted to provide for an increased $H_2$ content of the syngas. As another example, the CPO operational parameters can be adjusted to provide for a decreased $CO_2$ content of the syngas. As yet another example, the CPO operational parameters can be adjusted to provide for a decreased unreacted hydrocarbons (e.g., unreacted $CH_4$) content of the syngas.

In embodiments, the CPO reactor 10 is characterized by at least one CPO operational parameter selected from the group consisting of a CPO inlet temperature of from about 200° C. to about 550° C.; a CPO outlet temperature of from about 600° C. to about 1,400° C.; a CPO pressure of from about 1 barg to about 90 barg; a CPO contact time of from about 0.001 milliseconds (ms) to about 5 seconds (s); a carbon to oxygen (C/O) molar ratio in the CPO reactant mixture of from about 1.5:1 to about 2.5:1, wherein the C/O molar ratio refers to the total moles of carbon (C) of hydrocarbons in the reactant mixture divided by the total moles of oxygen ($O_2$) in the reactant mixture; a steam to carbon (S/C) molar ratio in the CPO reactant mixture of from about 0 to about 2:1, wherein the S/C molar ratio refers to the total moles of water ($H_2O$) in the reactant mixture divided by the total moles of carbon (C) of hydrocarbons in the reactant mixture; and combinations thereof. In embodiments, the CPO reactor 10 is characterized by a steam to carbon (S/C) molar ratio in the CPO reactant mixture of from about 0.05:1 to about 1:1, from about 0.1:1 to about 2:1, from about 0.1:1 to about 2:1, or equal to about 0.1, 0.2, 0.3, 0.4, 0.5, 0.6, 0.7, 0.8, 0.9, or 1.0.

The CPO reaction is an exothermic reaction (e.g., heterogeneous catalytic reaction; exothermic heterogeneous catalytic reaction) that is generally conducted in the presence of a CPO catalyst comprising a catalytically active metal, i.e., a metal active for catalyzing the CPO reaction. The catalytically active metal can comprise a noble metal (e.g., Pt, Rh, Ir, Pd, Ru, Ag, and the like, or combinations thereof); a non-noble metal (e.g., Ni, Co, V, Mo, P, Fe, Cu, and the like, or combinations thereof); rare earth elements (e.g., La, Ce, Nd, Eu, and the like, or combinations thereof); oxides thereof; and the like; or combinations thereof. Generally, a noble metal is a metal that resists corrosion and oxidation in a water-containing environment. As will be appreciated by one of skill in the art, and with the help of this disclosure, the components of the CPO catalyst (e.g., metals such as noble metals, non-noble metals, rare earth elements) can be either phase segregated or combined within the same phase.

In embodiments, the CPO catalysts suitable for use in the present disclosure can be supported catalysts and/or unsupported catalysts. In some embodiments, the supported catalysts can comprise a support, wherein the support can be catalytically active (e.g., the support can catalyze a CPO reaction). For example, the catalytically active support can comprise a metal gauze or wire mesh (e.g., Pt gauze or wire mesh); a catalytically active metal monolithic catalyst; etc. In other embodiments, the supported catalysts can comprise a support, wherein the support can be catalytically inactive (e.g., the support cannot catalyze a CPO reaction), such as $SiO_2$; silicon carbide (SiC); alumina; a catalytically inactive monolithic support; etc. In yet other embodiments, the supported catalysts can comprise a catalytically active support and a catalytically inactive support.

In some embodiments, a CPO catalyst can be wash coated onto a support, wherein the support can be catalytically active or inactive, and wherein the support can be a monolith, a foam, an irregular catalyst particle, etc.

In some embodiments, the CPO catalyst can be a monolith, a foam, a powder, a particle, etc. Nonlimiting examples of CPO catalyst particle shapes suitable for use in the present disclosure include cylindrical, discoidal, spherical, tabular, ellipsoidal, equant, irregular, cubic, acicular, and the like, or combinations thereof.

In some embodiments, the support comprises an inorganic oxide, alpha, beta or theta alumina ($Al_2O_3$), activated $Al_2O_3$, silicon dioxide ($SiO_2$), titanium dioxide ($TiO_2$), magnesium oxide (MgO), zirconium oxide ($ZrO_2$), lanthanum (III) oxide ($La_2O_3$), yttrium (III) oxide ($Y_2O_3$), cerium (IV) oxide ($CeO_2$), zeolites, ZSM-5, perovskite oxides, hydrotalcite oxides, and the like, or combinations thereof.

Without limitation, CPO processes, CPO reactors, CPO catalysts, and CPO catalyst bed configurations suitable for use in the present disclosure are described in more detail in U.S. Provisional Patent Application No. 62/522,910 filed Jun. 21, 2017 (International Application No. PCT/IB2018/054475 filed Jun. 18, 2018) and entitled "Improved Reactor Designs for Heterogeneous Catalytic Reactions;" and U.S. Provisional Patent Application No. 62/521,831 filed Jun. 19, 2017 (International Application No. PCT/IB2018/054470 filed Jun. 18, 2018) and entitled "An Improved Process for Syngas Production for Petrochemical Applications;" each of which is hereby incorporated herein by reference in its entirety for purposes not contrary to this disclosure.

According to embodiments of this disclosure, a CPO reactor effluent 15 is recovered from the CPO reactor 10, wherein the CPO reactor effluent 15 comprises hydrogen, carbon monoxide, water, carbon dioxide, and unreacted hydrocarbons. In embodiments, the CPO reactor effluent 15 can be characterized by an M ratio of greater than or equal to about 1.5, alternatively greater than or equal to about 1.6, alternatively greater than or equal to about 1.7, alternatively greater than or equal to about 1.8, alternatively greater than or equal to about 1.84, alternatively greater than or equal to about 1.9, alternatively from about 1.5 to about 1.95, alternatively from about 1.7 to about 2.3, alternatively from about 1.8 to about 2.2, or alternatively from about 1.9 to about 2.2.

The CPO reactor effluent 15 as disclosed herein can be characterized by a $H_2/CO$ molar ratio of greater than about 1.7, alternatively greater than about 1.8, alternatively greater than about 1.9, alternatively greater than about 2.0, or alternatively greater than about 2.1. In some embodiments, the CPO reactor effluent 15 as disclosed herein can be characterized by a $H_2/CO$ molar ratio of from about 1.7 to about 2.3, alternatively from about 1.75 to about 1.81, alternatively from about 1.8 to about 2.2, or alternatively from about 1.9 to about 2.1.

In embodiments, the CPO reactor effluent 15 can have a $CO_2$ content of less than about 10 mol %, less than about 9 mol %, less than about 8 mol %, less than about 7 mol %, alternatively less than about 6 mol %, alternatively less than about 5 mol %, alternatively less than about 4 mol %, alternatively less than about 3 mol %, alternatively less than about 2 mol %, alternatively less than about 1 mol %, alternatively greater than about 0.1 mol %, alternatively greater than about 0.25 mol %, alternatively greater than about 0.5 mol %, alternatively from about 0.1 mol % to about 7 mol %, alternatively from about 0.25 mol % to about 6 mol %, or alternatively from about 0.5 mol % to about 5 mol %.

In embodiments, water can be condensed and separated from at least a portion of the CPO reactor effluent 15, e.g., in a condenser. In embodiments, the CPO reactor effluent 15 can be subjected to processing, such as the recovery of unreacted hydrocarbons, diluent, water, etc. In embodiments, a process as disclosed herein can further comprise: (i) recovering at least a portion of the unreacted hydrocarbons from the CPO reactor effluent 15 to yield recovered hydrocarbons, and (ii) recycling at least a portion of the recovered hydrocarbons to the CPO reactor 10. As will be appreciated by one of skill in the art, and with the help of this disclosure, although fairly high conversions can be achieved in CPO processes (e.g., conversions of greater than or equal to about 90%), the unconverted hydrocarbons could be recovered and recycled back to the CPO reactor 10.

In embodiments, a process of this disclosure further comprises cooling the CPO reactor effluent 15 by heating the hydrocarbons of first portion 5A while cooling the CPO reactor effluent 15. Cooling the CPO reactor effluent 15 by heating the hydrocarbons of first portion 5A while cooling the CPO reactor effluent 15 can comprise exchanging heat between the CPO reactor effluent 15 and a heat exchange fluid 18 (e.g., water or low pressure (LP) steam) in a first heat exchanger HE1 to yield a first cooled CPO reactor effluent 15A; heating the hydrocarbons while further cooling the first cooled CPO reactor effluent 15A via heat exchange therebetween in a second heat exchanger HE2 to yield heated hydrocarbons 5A' and a second cooled CPO reactor effluent 15B and LP steam, medium pressure (MP) steam, and/or high pressure (HP) steam. In embodiments, the method further comprises optionally heating the hydrocarbons prior to via an electrical heater or heat exchanger HE5 upstream of second heat exchanger HE2.

In embodiments, the heated first portion of hydrocarbons 5A' is introduced directly into CPO reactor 10. In alternate embodiments, the first portion 5A of hydrocarbons is heated prior to desulfurization. In embodiments, the heated first portion of hydrocarbons 5A' comprise one or more sulfur-containing compounds, and the process comprises removing at least a portion of the sulfur-containing compounds from the heated first portion of hydrocarbons 5A' to yield a desulfurized first portion of hydrocarbons 8, which can be introduced directly into CPO reactor 10 or can be introduced into CPO reactor 10 following heat exchange in a fourth heat exchanger HE4, as described further below.

In embodiments, the herein disclosed process further comprises cooling desulfurized first portion of hydrocarbons 8. For example, in embodiments, the desulfurized first portion of hydrocarbons 8 is cooled by heating water 9 while cooling the desulfurized first portion of hydrocarbons 8 by heat exchange in a fourth heat exchanger HE4 to yield steam 11 (e.g., LP steam) and cooled desulfurized first portion of hydrocarbons 8'. In embodiments, at least a portion of the cooled desulfurized first portion of hydrocarbons 8' and optionally at least a portion 11A of the steam 11 are fed to the CPO reactor 10 as a component of the CPO reactant mixture in step (a).

In embodiments, cooling the CPO reactor effluent 15 further comprises heating water 16 while cooling the second cooled CPO reactor effluent 15B by heat exchange in a third heat exchanger HE3 to yield stream 17 (e.g., comprising boiled water and/or LP steam) and a third cooled CPO reactor effluent 15C. In embodiments, at least a portion of the third cooled CPO reactor effluent 15C is fed to the WGS reactor 20 in step (b), described further hereinbelow. The stream 17 can be low pressure steam. In embodiments, at least a portion 21 of the steam (17/19) is utilized to power a steam-driven compressor, such as a syngas compressor 30 described further hereinbelow.

As noted hereinabove, in embodiments, a process of this disclosure further comprises (b) feeding at least a portion of the CPO reactor effluent 15 to a water-gas shift (WGS) reactor 20 to produce a hydrogen enriched reactor effluent 15D, wherein a portion of the carbon monoxide of the CPO reactor effluent 15 reacts with water via a WGS reaction to produce hydrogen and carbon dioxide, wherein the hydrogen enriched reactor effluent 15D is characterized by a $H_2/CO$ molar ratio of the hydrogen enriched reactor effluent and by an M ratio of the hydrogen enriched reactor effluent, and wherein the $H_2/CO$ molar ratio of the hydrogen enriched reactor effluent 15D is greater than the $H_2/CO$ molar ratio of the CPO reactor effluent 15. As described hereinabove, the CPO reactor effluent 15 can be utilized to preheat the first portion 5A of the hydrocarbon feed 5 to provide heated first portion 5A' of the hydrocarbons in a first heat exchanger HE1, and/or to produce steam (e.g., high pressure (HP) steam in HP steam stream 17) from water or steam 16 via third heat exchanger HE3 prior to introduction into WGS reactor 20. Thus, in embodiments, a process of this disclosure comprises feeding at least a portion of the cooled CPO reactor effluent (e.g., first cooled CPO reactor effluent 15B and/or second cooled CPO reactor effluent 15C) to a water-gas shift (WGS) reactor 20 to produce a hydrogen enriched reactor effluent 15D, wherein a portion of the carbon monoxide of the cooled CPO reactor effluent reacts with water via a WGS reaction to produce hydrogen and carbon dioxide, wherein the hydrogen enriched reactor effluent 15D is characterized by a $H_2/CO$ molar ratio of the hydrogen enriched reactor effluent 15D, wherein the hydrogen enriched reactor effluent 15D is characterized by an M ratio of the hydrogen enriched reactor effluent 15D, and wherein the $H_2/CO$ molar ratio of the hydrogen enriched reactor effluent 15D is greater than the $H_2/CO$ molar ratio of the CPO reactor effluent 15, the first cooled CPO reactor effluent 15B, and/or the second cooled CPO reactor effluent 15C.

Within the water-gas shift (WGS) reactor 20, a portion of the carbon monoxide of the CPO reactor effluent 15 reacts with water via a WGS reaction to produce hydrogen and carbon dioxide and thus provide hydrogen enriched syngas as hydrogen enriched reactor effluent 15D. Generally, the WGS reaction describes the catalytic reaction of carbon monoxide and water vapor to form carbon dioxide and hydrogen, for example as represented by Equation (2):

$$CO + H_2O \rightleftharpoons CO_2 + H_2 \qquad (2)$$

The WGS reaction can be used to increase the $H_2/CO$ molar ratio of gas streams comprising carbon monoxide and hydrogen. WGS catalysts can comprise any suitable WGS catalysts, such as commercial WGS catalysts; chromium or copper promoted iron-based catalysts; copper-zinc-aluminum catalyst; and the like; or combinations thereof.

A portion of the carbon monoxide in the CPO reactor can undergo a WGS reaction (as represented by equation (2)) within CPO reactor 10, thereby increasing the amount of hydrogen in the CPO reactor effluent 15.

In embodiments, a process for producing syngas as disclosed herein can further comprise recovering a hydrogen enriched reactor effluent 15D from the WGS reactor 20, wherein the hydrogen enriched reactor effluent 15D comprises hydrogen, carbon monoxide, carbon dioxide, water, and unreacted hydrocarbons, and wherein the $H_2/CO$ molar ratio of the hydrogen enriched WGS reactor effluent 15D is greater than the $H_2/CO$ molar ratio of the CPO reactor effluent 15.

In embodiments, the hydrogen enriched WGS reactor effluent 15D can be used as syngas in a downstream process without further processing the WGS reactor effluent. In other embodiments, the hydrogen enriched WGS reactor effluent 15D can be further processed prior to downstream chemical (e.g., methanol) synthesis. For example, in embodiments, the hydrogen enriched WGS reactor effluent 15D can be further processed in a carbon dioxide separator 25 to reduce its carbon dioxide content.

In embodiments, a process of this disclosure further comprises removing a portion of the $CO_2$ from the hydrogen enriched reactor effluent 15D in a $CO_2$ separator 25 to yield the syngas 15E. The resulting syngas 15E is characterized by an M ratio of the syngas, wherein the M ratio of the syngas 15E is greater than the M ratio of the CPO reactor effluent 15, and wherein the M ratio of the syngas 15E is greater than the M ratio of the hydrogen enriched reactor effluent 15D.

In embodiments, the CPO reactor effluent 15 is further processed to produce a hydrogen enriched syngas 15E by removing at least a portion of the carbon dioxide from the CPO reactor effluent 15 and/or the hydrogen enriched WGS reactor effluent 15D to yield the hydrogen enriched syngas 15E. As will be appreciated by one of skill in the art, and with the help of this disclosure, and without wishing to be limited by theory, while the $H_2/CO$ molar ratio of the syngas does not change by removing carbon dioxide from the syngas, the concentration of hydrogen increases in the syngas by removing carbon dioxide from the syngas. However, the M ratio of the syngas changes with changing the carbon dioxide content of the syngas, wherein the M ratio is a molar ratio defined as $(H_2-CO_2)/(CO+CO_2)$. The CPO reactor effluent 15 is characterized by an M ratio of the CPO reactor effluent. The hydrogen enriched syngas 15E is characterized by an M ratio of the hydrogen enriched syngas. The hydrogen enriched syngas 15E is characterized by an M ratio that is greater than the M ratio of the CPO reactor effluent 15 and also greater than the M ratio of the hydrogen enriched WGS reactor effluent 15D. As will be appreciated by one of skill in the art, and with the help of this disclosure, a $CO_2$-lean syngas has a higher M ratio than a $CO_2$-rich syngas: the lower the $CO_2$ content of the syngas, the higher the M ratio of the syngas.

In embodiments, at least a portion of the carbon dioxide can be removed from the hydrogen enriched WGS reactor effluent 15D to provide a syngas 15E suitable for downstream chemical synthesis. As syngas 15E is hydrogen enriched relative to CPO reactor effluent 15, it may also be referred to herein as a 'hydrogen enriched syngas'. By reducing the carbon dioxide content in $CO_2$ separator 25, the resulting syngas 15E is characterized by an M ratio that is greater than the M ratio of the hydrogen enriched WGS reactor effluent 15D.

In embodiments, the hydrogen enriched syngas 15E can be characterized by an M ratio of greater than or equal to about 1.7, 1.9, 2.1, 2.3, or 2.5, from about 1.9 to about 2.2, alternatively from about 1.95 to about 2.1, or alternatively from about 1.98 to about 2.06. In embodiments, the hydrogen enriched syngas 15E can be characterized by a $H_2/CO$ molar ratio of greater than or equal to about 1.8, 2.0, 2.2, 2.5, 2.8, or 3 or from about 1.5 to about 3.5, alternatively from about 2 to about 3 or alternatively from about 2.25 to about 2.75. The $H_2/CO$ molar ratio of the hydrogen enriched WGS reactor effluent 15D and the hydrogen enriched syngas 15E can be substantially the same.

$CO_2$ separator 25 can comprise any $CO_2$ separator known to those of skill in the art to be operable to remove $CO_2$ from the hydrogen enriched reactor effluent 15D to yield the syngas 15E. The $CO_2$ separator 25 can comprise $CO_2$ removal by amine (e.g., monoethanolamine) absorption (e.g., amine scrubbing), pressure swing adsorption (PSA), temperature swing adsorption, gas separation membranes (e.g., porous inorganic membranes, palladium membranes, polymeric membranes, zeolites, etc.), cryogenic separation, and the like, or combinations thereof. In embodiments, the step of removing at least a portion of the carbon dioxide from the CPO reactor effluent 15 and/or the hydrogen enriched WGS reactor effluent 15D to yield the hydrogen enriched syngas 15E can comprise $CO_2$ removal by amine absorption. For example, $CO_2$ separator 25 can comprise a $CO_2$ scrubber, such as an amine unit. In embodiments, less than about 50, 45, 40, 35, or 30 mol % of the $CO_2$ in the hydrogen enriched WGS reactor effluent 15D is removed in the $CO_2$ separator 25 to yield the syngas 15E.

In embodiments, a first portion of the CPO reactor effluent 15 can be introduced to the WGS reactor 20 to produce the hydrogen enriched WGS reactor effluent 15D. In such embodiments, at least a portion of the hydrogen enriched WGS reactor effluent 15D can be contacted with a second portion of the CPO reactor effluent 15 to yield a hydrogen enriched syngas. In such embodiments, the CPO reactor effluent (e.g., first portion of the CPO reactor effluent 15, second portion of the CPO reactor effluent 15) and/or the hydrogen enriched WGS reactor effluent 15D can be subjected to a step of carbon dioxide removal. For example, the first portion of the CPO reactor effluent 15 that can be introduced to the WGS reactor 20 to produce the hydrogen enriched WGS reactor effluent 15D can be from about 0.01 vol. % to about 100 vol. %, alternatively from about 0.1 vol. % to about 90 vol. %, alternatively from about 1 vol. % to about 80 vol. %, alternatively from about 10 vol. % to about 75 vol. %, alternatively from about 20 vol. % to about 60 vol. %, alternatively from about 25 vol. % to about 50 vol. %, alternatively greater than or equal to about 5 vol. %, alternatively greater than or equal to about 10 vol. %, alternatively greater than or equal to about 15 vol. %, alternatively greater than or equal to about 20 vol. %, or alternatively greater than or equal to about 25 vol. %, based on the total volume of the CPO reactor effluent 15.

In embodiments, a second portion of the CPO reactor effluent 15 can be contacted with at least a portion of the hydrogen enriched WGS reactor effluent 15D to produce a combined effluent stream, wherein the combined effluent stream is characterized by an M ratio of the combined effluent stream; wherein at least a portion of the carbon dioxide can be removed from the combined effluent stream in $CO_2$ separator 25 to yield the syngas 15E, and wherein the syngas 15E is characterized by an M ratio that is greater than the M ratio of the combined effluent stream. For example, the second portion of the CPO reactor effluent 15 that can be contacted with at least a portion of the hydrogen enriched WGS reactor effluent 15D to produce a combined effluent stream can be from about 0.01 vol. % to about 99.99 vol. %, alternatively from about 10 vol. % to about 99.9 vol. %, alternatively from about 20 vol. % to about 99 vol. %, alternatively from about 25 vol. % to about 90 vol. %, alternatively from about 40 vol. % to about 80 vol. %, alternatively from about 50 vol. % to about 75 vol. %, alternatively less than about 95 vol. %, alternatively less than about 90 vol. %, alternatively less than about 85 vol. %, alternatively less than about 80 vol. %, or alternatively less than about 75 vol. %, based on the total volume of the CPO reactor effluent 15.

In embodiments, a process for producing syngas as disclosed herein can comprise a step of removing carbon dioxide from one or more streams; e.g., carbon dioxide can be removed from at least a portion of the CPO reactor effluent 15, from at least a portion of the hydrogen enriched WGS reactor effluent 15D, from at least a portion of the combined effluent stream, etc. For example, carbon dioxide can be removed from at least a portion of the CPO reactor effluent 15 and/or from at least a portion of the hydrogen enriched WGS reactor effluent 15D to yield the syngas 15E; carbon dioxide can be removed from either at least a portion of the CPO reactor effluent 15 or from at least a portion of the hydrogen enriched WGS reactor effluent 15D, prior to combining the CPO reactor effluent 15 and the hydrogen enriched WGS reactor effluent 15D to yield the syngas 15E; carbon dioxide can be removed from the combined effluent stream to yield the syngas 15E; and the like; or combinations thereof.

Methanol synthesis can be effected in a methanol synthesis loop 40. Methanol synthesis loop 40 can comprise any methanol synthesis loop known in the art and with the help of this disclosure to be suitable for producing crude methanol stream 55 and a purge gas stream 56. For example, the methanol synthesis loop 40 can comprise one or more methanol synthesis reactors, one or more gas-liquid separators, one or more heat exchangers, one or more recycle streams, and/or one or more steam drums. In embodiments, a process for producing methanol as disclosed herein can comprise a step of feeding at least a portion of the syngas 15E to a methanol synthesis loop 40. Methanol synthesis loop 40 is operable to produce a crude methanol stream 55 and a purge gas stream 56. The methanol synthesis loop comprises a methanol synthesis reactor or 'methanol reactor' operable to produce a methanol reactor effluent stream. The methanol reactor effluent stream comprises methanol, water, $H_2$, CO, $CO_2$, and hydrocarbons. The methanol synthesis loop 40 can comprise any reactor suitable for a methanol synthesis reaction from CO and $H_2$, such as for example a trickle bed reactor, a fluidized bed reactor, a slurry reactor, a loop reactor, a cooled multi tubular reactor, and the like, or combinations thereof.

Generally, CO and $H_2$ can be converted into methanol ($CH_3OH$), for example as represented by Equation (3):

$$CO + H_2 \rightleftharpoons CH_3OH \quad (3)$$

$CO_2$ and $H_2$ can also be converted to methanol, for example as represented by Equation (4):

$$CO_2 + 3H_2 \rightleftharpoons CH_3OH + H_2O \quad (4)$$

Without wishing to be limited by theory, the lower the $CO_2$ content of the syngas 15E, the lower the amount of water produced in the methanol reactor. As will be appreciated by one of skill in the art, and with the help of this disclosure, syngas produced by SMR has a fairly high content of hydrogen (as compared to the hydrogen content of syngas produced by CPO), and a syngas with an elevated hydrogen content can promote the $CO_2$ conversion to methanol, for example as represented by Equation (4), which in turn can lead to an increased water content in a crude methanol stream (e.g., crude methanol stream 55, described hereinbelow).

Methanol synthesis from CO, $CO_2$ and $H_2$ is a catalytic process, and is most often conducted in the presence of copper based catalysts. The methanol synthesis reactor can comprise a methanol production catalyst, such as any suitable commercial catalyst used for methanol synthesis. Non-limiting examples of methanol production catalysts suitable for use in the methanol reactor of methanol synthesis loop 40 in the current disclosure include Cu, Cu/ZnO, $Cu/ThO_2$, $Cu/Zn/Al_2O_3$, $Cu/ZnO/Al_2O_3$, Cu/Zr, and the like, or combinations thereof.

In embodiments, a process for producing methanol as disclosed herein can comprise a step of compressing at least a portion of the syngas 15E in a syngas compressor 30 to yield a compressed syngas 15E', and at least a portion of the compressed syngas 15E' is fed to the methanol synthesis loop 40. In embodiments, the compressor 30 is a steam-driven compressor, and at least a portion 17A of the (e.g., HP) steam 17 is used in a turbine for the steam-driven compressor. In embodiments, the compressor 30 is a steam-driven compressor, and at least a portion of the second portion 5B of the hydrocarbon feed 5 is utilized to provide steam for powering the steam-driven compressor. In embodiments, steam (e.g., additional or alternate steam) is generated via combustion of alternate hydrocarbons, and the steam is further used to power the steam-driven compressor. As noted above, in embodiments, the syngas 15E and/or compressed syngas 15E' fed to methanol synthesis loop 40 is characterized by a $H_2/CO$ molar ratio of greater than or equal to about 1.8, 2.0, 2.2, 2.5, 2.8, or 3 and/or an M ratio of greater than or equal to about 1.7, 1.9, 2.1, 2.3, or 2.5

In embodiments, methanol loop 40 utilizes a series (e.g., 3, 4, or 5) of quenched bed reactors, and cold feed is mixed with the exit gas from each bed to lower the gas temperature before the feed is passed to the subsequent bed. Due to increased carbon monoxide concentration in the methanol reactor loop according to this disclosure, the temperature of the exit gas from each bed may be higher than in methanol synthesis plants employing SMR alone. Accordingly, in embodiments, the temperature of the cold feed streams injected between the beds can be lowered until an adiabatic operation in the methanol synthesis reactor is achieved.

In embodiments, a process for producing methanol as disclosed herein can comprise a step of introducing at least a portion of the methanol reactor effluent stream to a separator to produce the crude methanol stream 55 and a vapor stream, wherein the crude methanol stream 55 comprises methanol and water, and wherein the vapor stream comprises H$_2$, CO, CO$_2$, and hydrocarbons. The methanol reactor effluent stream can be separated into the crude methanol stream 55 and the vapor stream in a gas-liquid separator, for example, such as a vapor-liquid separator, flash drum, knock-out drum, knock-out pot, compressor suction drum, etc.

In embodiments, a process for producing methanol as disclosed herein can comprise a step of separating at least a portion of the crude methanol stream 55 from the methanol synthesis loop in a distillation unit 60 into a methanol stream 65 and a water stream 66. The distillation unit 60 can comprise one or more distillation columns. The water stream 66 comprises water and residual methanol. Generally, the one or more distillation columns can separate components of the crude methanol stream 55 based on their boiling points. As will be appreciated by one of skill in the art, and with the help of this disclosure, the higher the water content of the crude methanol stream 55, the more distillation columns are necessary to purify the methanol.

In embodiments, the methanol stream 65 can comprise methanol in an amount of greater than or equal to about 95 wt %, alternatively greater than or equal to about 97.5 wt %, alternatively greater than or equal to about 99 wt %, or alternatively greater than or equal to about 99.9 wt %, based on the total weight of the methanol stream 65.

In embodiments, a process for producing methanol as disclosed herein can comprise a step of recycling a first portion of the vapor stream to the methanol synthesis loop 40 (e.g., to a methanol synthesis reactor thereof), and introducing a second portion of the vapor stream, as purge gas stream 56, to a hydrogen separation unit 70 to produce a hydrogen stream 71 and a residual gas stream 72. In embodiments, the second portion (e.g., purge gas stream 56) of the vapor stream is from about 90 weight percent (wt %) % to about 99 wt %, from about 94 wt % to about 97 wt %, or from about 92 wt % to about 99 wt % of the vapor stream, based on the total weight of the vapor stream. In embodiments, the first portion of the vapor stream recycled within the methanol synthesis loop 40 is from about 1 weight percent (wt %) % to about 10 wt %, from about 2 wt % to about 9 wt %, or from about 3 wt % to about 6 wt % of the vapor stream.

Hydrogen separator 70 can be any apparatus known in the art to be operable to separate a substantially pure (e.g., pure) hydrogen stream 71 from the purge gas stream 56 introduced thereto. Hydrogen separator 70 can partially or fully remove hydrogen from the purge gas stream 56 introduced thereto. In embodiments, the hydrogen stream 71 is split, whereby at least a portion of hydrogen stream 71 can be recycled as first recycle 71A to the CPO reactor 10 (e.g., upstream of HDS 6, such as via heat exchanged first portion 5N) and/or at least a portion of hydrogen stream 71 can be recycled as second recycle 71B to methanol synthesis loop 40 (e.g., to the methanol synthesis reactor(s)) with reformed synthesis gas (e.g., syngas 15E). In embodiments, the residual gas stream 72 is split, whereby at least a portion of residual gas stream 72 can be recycled as residual gas recycle 72B to the CPO reactor 10 (e.g., upstream of HDS 6, such as via heat exchanged first portion 5A') and/or at least a portion of residual gas stream 72 can be utilized as remaining residual gas stream 72A as fuel.

In embodiments, the syngas and/or methanol synthesis system and process of this disclosure exclude a steam methane reforming (SMR) reactor. In embodiments, the methanol reactor of methanol synthesis loop 40 is characterized by a methanol reactor volume that is decreased when compared to the volume of a methanol reactor used in an otherwise similar process that produces (the same production of) methanol from syngas generated via a steam methane reforming (SMR) reactor without a CPO reactor. In embodiments, the methanol reactor is characterized by a methanol reactor volume that is the same as the volume of a methanol reactor used in an otherwise similar process that produces methanol via a steam methane reforming (SMR) reactor without a CPO reactor, and the herein disclosed process produces a greater amount of methanol for a given amount of hydrocarbon feed 5.

In embodiments, a process for producing methanol as disclosed herein can advantageously display improvements in one or more process characteristics when compared to conventional processes. In embodiments, a methanol synthesis process of this disclosure provides for an increased carbon efficiency, a reduced methanol reactor size due to lower syngas flow (or increased methanol production for a same methanol reactor size), a reduced energy intensity, a higher overall efficiency, a higher chemical carbon efficiency, a reduced syngas compressor duty, a higher methanol loop efficiency, a reduced steam usage, or a combination thereof relative to an otherwise similar process that utilizes an SMR to generate the syngas for methanol synthesis.

By utilizing CPO, along with WGS, CO$_2$ removal, and/or heat integration (e.g., via heat exchangers HE1, HE2, HE3, HE4 and/or HE5), rather than an SMR to provide a synthesis gas suitable for downstream methanol synthesis, the herein disclosed system and process allow for a reduced energy utilization with minimal capital expenditures for a new or retrofit application. In embodiments, a methanol synthesis plant of this disclosure provides for an energy intensity reduction from an indexed value of from about 90 to 100 MMBTU/ton of methanol to an indexed value of from about 20 to 50 MMBTU/ton of methanol, which represents a reduction of from about 40% to 80%. In embodiments, CPO, WGS, and/or CO$_2$ removal are utilized in conjunction with heat integration (e.g., via heat exchangers HE1, HE2, HE3, HE4 and/or HE5) to provide a syngas suitable for downstream methanol synthesis (or synthesis of another chemical for which a reduced H2/CO molar ratio is desirable) without the utilization of SMR. In embodiments, the herein disclosed CPO process enables the reduction of the overall energy intensity or carbon efficiency of a methanol plant (e.g., by from about 5 to about 15%) compared to state of the art methanol plant technologies (e.g., that utilize combined reforming, ATR, and ATR+gas heated reforming (GHR)).

A process according to this disclosure can generate higher heat from the methanol synthesis reactor of methanol synthesis loop 40, which heat can be utilized within the process (e.g., additional medium pressure or low pressure steam to be used in the process).

As will be appreciated by one of skill in the art, and with the help of this disclosure, since the CPO reaction is exothermic, very little heat supply in the form of fuel combustion is needed (e.g., for pre-heating reactants in the reaction mixture that is supplied to a syngas generation section), when compared to conventional steam reforming. As such, the process for producing methanol utilizing CPO syngas as disclosed herein can advantageously generate less CO$_2$ through fuel burning, when compared to steam reforming.

Additional advantages of the processes for the production methanol as disclosed herein can be apparent to one of skill in the art viewing this disclosure.

While various embodiments have been shown and described, modifications thereof can be made by one skilled in the art without departing from the spirit and teachings of the disclosure. The embodiments described herein are exemplary only, and are not intended to be limiting. Many variations and modifications of the subject matter disclosed herein are possible and are within the scope of the disclosure. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). For example, whenever a numerical range with a lower limit, $R_L$ and an upper limit, $R_U$ is disclosed, any number falling within the range is specifically disclosed. In particular, the following numbers within the range are specifically disclosed: $R=R_L+k*(R_U-R_L)$, wherein k is a variable ranging from 1 percent to 100 percent with a 1 percent increment, i.e., k is 1 percent, 2 percent, 3 percent, 4 percent, 5 percent, . . . 50 percent, 51 percent, 52 percent, . . . , 95 percent, 96 percent, 97 percent, 98 percent, 99 percent, or 100 percent. Moreover, any numerical range defined by two R numbers as defined in the above is also specifically disclosed. Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, etc.

Accordingly, the scope of protection is not limited by the description set out above but is only limited by the claims which follow, that scope including all equivalents of the subject matter of the claims. Each and every claim is incorporated into the specification as an embodiment of the present disclosure. Thus, the claims are a further description and are an addition to the embodiments of the present disclosure. The discussion of a reference is not an admission that it is prior art to the present disclosure, especially any reference that may have a publication date after the priority date of this application. The disclosures of all patents, patent applications, and publications cited herein are hereby incorporated by reference, to the extent that they provide exemplary, procedural, or other details supplementary to those set forth herein.

ADDITIONAL DESCRIPTION

The particular embodiments disclosed above are illustrative only, as the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present disclosure. Alternative embodiments that result from combining, integrating, and/or omitting features of the embodiment(s) are also within the scope of the disclosure. While compositions and processes are described in broader terms of "having", "comprising," "containing," or "including" various components or steps, the compositions and processes can also "consist essentially of" or "consist of" the various components and steps. Use of the term "optionally" with respect to any element of a claim means that the element is required, or alternatively, the element is not required, both alternatives being within the scope of the claim.

Numbers and ranges disclosed above may vary by some amount. Whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an", as used in the claims, are defined herein to mean one or more than one of the element that it introduces. If there is any conflict in the usages of a word or term in this specification and one or more patent or other documents, the definitions that are consistent with this specification should be adopted.

Embodiments disclosed herein include:

A: A process for producing syngas comprising: (a) reacting, via a catalytic partial oxidation (CPO) reaction, a CPO reactant mixture in a CPO reactor to produce a CPO reactor effluent; wherein the CPO reactant mixture comprises hydrocarbons, oxygen, and optionally water; wherein the CPO reactor comprises a CPO catalyst; wherein the CPO reactor effluent comprises hydrogen ($H_2$), carbon monoxide (CO), carbon dioxide ($CO_2$), water, and unreacted hydrocarbons, wherein the CPO reactor effluent is characterized by a hydrogen to carbon monoxide ($H_2/CO$) molar ratio of the CPO reactor effluent, and wherein the CPO reactor effluent is characterized by an M ratio of the CPO reactor effluent, wherein the M ratio is a molar ratio defined as $(H_2-CO_2)/(CO+CO_2)$; (b) feeding at least a portion of the CPO reactor effluent to a water-gas shift (WGS) reactor to produce a hydrogen enriched reactor effluent, wherein a portion of the carbon monoxide of the CPO reactor effluent reacts with water via a WGS reaction to produce hydrogen and carbon dioxide, wherein the hydrogen enriched reactor effluent is characterized by a $H_2/CO$ molar ratio of the hydrogen enriched reactor effluent, wherein the hydrogen enriched reactor effluent is characterized by an M ratio of the hydrogen enriched reactor effluent, and wherein the $H_2/CO$ molar ratio of the hydrogen enriched reactor effluent is greater than the $H_2/CO$ molar ratio of the CPO reactor effluent; and (c) removing a portion of the $CO_2$ from the hydrogen enriched reactor effluent in a $CO_2$ separator to yield the syngas, wherein the syngas is characterized by an M ratio of the syngas, and wherein the M ratio of the syngas is greater than the M ratio of the CPO reactor effluent, and wherein the M ratio of the syngas is greater than the M ratio of the hydrogen enriched reactor effluent.

B: A process for producing methanol comprising: (a) reacting, via a catalytic partial oxidation (CPO) reaction, a CPO reactant mixture in a CPO reactor to produce a CPO reactor effluent; wherein the CPO reactant mixture comprises hydrocarbons, oxygen, and optionally water; wherein the CPO reactor comprises a CPO catalyst; wherein the CPO reactor effluent comprises hydrogen ($H_2$), carbon monoxide (CO), carbon dioxide ($CO_2$), water, and unreacted hydrocarbons, wherein the CPO reactor effluent is characterized by a hydrogen to carbon monoxide ($H_2/CO$) molar ratio of the CPO reactor effluent, and wherein the CPO reactor effluent is characterized by an M ratio of the CPO reactor effluent, wherein the M ratio is a molar ratio defined as $(H_2-CO_2)/(CO+CO_2)$; (b) heating water while cooling the CPO reactor effluent by heat exchange in a heat exchanger to yield steam and a cooled CPO reactor effluent; (c) feeding at least a portion of the cooled CPO reactor effluent to a water-gas shift (WGS) reactor to produce a hydrogen enriched reactor effluent, wherein a portion of the carbon monoxide of the cooled CPO reactor effluent reacts with water via a WGS reaction to produce hydrogen and carbon dioxide, wherein the hydrogen enriched reactor effluent is characterized by a $H_2/CO$ molar ratio of the hydrogen enriched reactor effluent, wherein the hydrogen enriched reactor effluent is characterized by an M ratio of the hydrogen enriched reactor effluent, and wherein the $H_2/CO$ molar ratio of the hydrogen enriched reactor effluent is greater than the $H_2/CO$ molar ratio of the CPO reactor effluent and/or the cooled CPO reactor effluent; (d) removing a portion of the $CO_2$ from the hydrogen enriched reactor effluent in a $CO_2$ separator to yield syngas, wherein the syngas is characterized by an M ratio of the syngas, and wherein the M ratio of the syngas is greater than the M ratio of the CPO reactor effluent, and wherein the M ratio of the syngas is greater than the M ratio of the hydrogen enriched reactor effluent; (e) powering a steam-driven compressor with at least a portion of the steam; (f) compressing at least a portion of the syngas in the steam-driven compressor to yield compressed syngas; (g) introducing at least a portion of the compressed syngas to a methanol synthesis loop to produce a crude methanol stream and a purge gas stream; wherein the crude methanol stream comprises methanol and water; and wherein the purge gas stream comprises hydrogen, carbon monoxide, carbon dioxide, and hydrocarbons; and (h) optionally generating additional steam via combustion of hydrocarbons, wherein the additional steam is further used to power the steam-driven compressor.

C: A system comprising: (a) a catalytic partial oxidation (CPO) reactor operable to produce, via a CPO reaction, a CPO reactor effluent comprising hydrogen ($H_2$), carbon monoxide (CO), carbon dioxide ($CO_2$), water, and unreacted hydrocarbons from a CPO reactant mixture comprising hydrocarbons, oxygen, and optionally water; wherein the CPO reactor effluent is characterized by a hydrogen to carbon monoxide ($H_2/CO$) molar ratio and an M ratio defined as $(H_2-CO_2)/(CO+CO_2)$; (b) a water-gas shift (WGS) reactor configured to produce, via a WGS reaction, a hydrogen enriched reactor effluent from at least a portion of the CPO reactor effluent, wherein the hydrogen enriched reactor effluent is characterized by a $H_2/CO$ molar ratio that is greater than the $H_2/CO$ molar ratio of the CPO reactor effluent; and (c) a $CO_2$ separator operable to remove a portion of the $CO_2$ from the hydrogen enriched reactor effluent to yield the syngas, wherein the syngas is characterized by an M ratio that is greater than the M ratio of the CPO reactor effluent and greater than the M ratio of the hydrogen enriched reactor effluent.

Each of embodiments A, B, and C may have one or more of the following additional elements: Element 1: wherein the hydrocarbons comprise methane, natural gas, natural gas liquids, associated gas, well head gas, enriched gas, paraffins, shale gas, shale liquids, fluid catalytic cracking (FCC) off gas, refinery process gases, stack gases, or combinations thereof. Element 2: wherein the hydrocarbons further comprise one or more sulfur-containing compounds, and wherein at least a portion of the sulfur-containing compounds is removed from the hydrocarbons prior to introducing the hydrocarbons to the CPO reactor. Element 3: wherein the CPO reactor is characterized by at least one CPO operational parameter selected from the group consisting of a CPO inlet temperature of from about 200° C. to about 550° C.; a CPO outlet temperature of from about 600° C. to about 1,400° C.; a CPO pressure of from about 1 barg to about 90 barg; a CPO contact time of from about 0.001 milliseconds (ms) to about 5 seconds (s); a carbon to oxygen (C/O) molar ratio in the CPO reactant mixture of from about 1.5:1 to about 2.5:1, wherein the C/O molar ratio refers to the total moles of carbon (C) of hydrocarbons in the reactant mixture divided by the total moles of oxygen ($O_2$) in the reactant mixture; a steam to carbon (S/C) molar ratio in the CPO reactant mixture of from about 0 to about 2:1, wherein the S/C molar ratio refers to the total moles of water ($H_2O$) in the reactant mixture divided by the total moles of carbon (C) of hydrocarbons in the reactant mixture; and combinations thereof. Element 4: wherein the M ratio of the syngas is greater than or equal to about 1.7. Element 5: wherein less than about 50 mol % of the $CO_2$ in the hydrogen enriched reactor effluent is removed in the $CO_2$ separator to yield the syngas. Element 6: further comprising cooling the CPO reactor effluent. Element 7: further comprising cooling the CPO reactor effluent and heating the hydrocarbons by: (i) exchanging heat between the CPO reactor effluent and a heat exchange fluid in a first heat exchanger to yield a first cooled CPO reactor effluent; (ii) heating the hydrocarbons while further cooling the first cooled CPO reactor effluent via heat exchange therebetween in a second heat exchanger to yield heated hydrocarbons and a second cooled CPO reactor effluent, wherein the heated hydrocarbons comprise one or more sulfur-containing compounds, and wherein at least a portion of the sulfur-containing compounds is removed from the heated hydrocarbons to yield desulfurized hydrocarbons; and (iii) optionally heating the hydrocarbons prior to (ii) via an electrical heater. Element 8: further comprising cooling the desulfurized hydrocarbons. Element 9: wherein cooling the desulfurized hydrocarbons comprises heating water while cooling the desulfurized hydrocarbons by heat exchange in a third heat exchanger to yield steam and cooled desulfurized hydrocarbons, wherein at least a portion of the cooled desulfurized hydrocarbons and optionally at least a portion of the steam are fed to the CPO reactor in step (a). Element 10: further comprising heating water while cooling the second cooled CPO reactor effluent by heat exchange in a third heat exchanger to yield a third cooled CPO reactor effluent, wherein at least a portion of the third cooled CPO reactor effluent is fed to the WGS reactor in step (b). Element 11: wherein at least a portion of a steam produced in the first heat exchanger and/or the third heat exchanger is optionally used to power a steam-driven compressor. Element 12: wherein at least a portion of the syngas is introduced to the steam-driven compressor to yield compressed syngas, and further comprising (i) introducing at least a portion of the compressed syngas to a methanol synthesis loop to produce a crude methanol stream and a purge gas stream; wherein the crude methanol stream comprises methanol and water; and wherein the purge gas stream comprises hydrogen, carbon monoxide, carbon dioxide, and hydrocarbons. Element 13: further comprising: introducing at least a portion of the purge gas stream to a hydrogen separation unit to produce a hydrogen stream and a residual gas stream; recycling at least a portion of the residual gas stream to the CPO reactor and/or utilizing at least a portion of the residual gas stream as fuel; and recycling at least a portion of the hydrogen stream to the methanol synthesis loop and/or recycling at least a portion of the hydrogen stream to the CPO reactor. Element 14: wherein the methanol synthesis loop comprises a methanol reactor that is characterized by a methanol reactor volume that is decreased when compared to the volume of a methanol reactor used in an otherwise similar process that produces methanol from syngas generated via a steam methane reforming (SMR) reactor without a CPO reactor. Element 15: excluding a steam methane reforming (SMR) reactor. Element 16: wherein the hydrocarbons combusted in step (h) are less than about 10 wt % of the total hydrocarbons, based on the total weight of the total hydrocarbons, and wherein the total hydrocarbons are given by the sum of the hydrocarbons introduced to the CPO reactor in step (a) and the hydrocarbons combusted in step (h). Element 17: wherein the CPO reactor is characterized by a steam to carbon (S/C) molar ratio in the CPO reactant mixture of from about 0.05:1 to about 1:1, wherein the S/C molar ratio refers to the total moles of water ($H_2O$) in the reactant mixture divided by the total moles of carbon (C) of hydrocarbons in the reactant mixture; and wherein the syngas and/or compressed syngas is characterized by a $H_2$/CO molar ratio of greater than or equal to about 1.8. Element 18: wherein the M ratio of the syngas and/or compressed syngas is greater than or equal to about 2.0. Element 19: further comprising a methanol synthesis loop operable to produce a crude methanol stream and a purge gas stream; wherein the crude methanol stream comprises methanol and water; and wherein the purge gas stream comprises hydrogen, carbon monoxide, carbon dioxide, and hydrocarbons. Element 20: further comprising a heat exchanger operable for transferring heat from the CPO reactor effluent to heat the CPO reactant mixture and/or a heat exchanger operable for transferring heat from the CPO reactor effluent to produce steam.

While preferred embodiments of the invention have been shown and described, modifications thereof can be made by one skilled in the art without departing from the teachings of this disclosure. The embodiments described herein are exemplary only, and are not intended to be limiting. Many variations and modifications of the invention disclosed herein are possible and are within the scope of the invention.

Numerous other modifications, equivalents, and alternatives, will become apparent to those skilled in the art once the above disclosure is fully appreciated. It is intended that the following claims be interpreted to embrace all such modifications, equivalents, and alternatives where applicable. Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the detailed description of the present invention. The disclosures of all patents, patent applications, and publications cited herein are hereby incorporated by reference.

What is claimed is:

1. A process for producing syngas comprising:
    (a) reacting, via a catalytic partial oxidation (CPO) reaction, a CPO reactant mixture in a CPO reactor to produce a CPO reactor effluent; wherein the CPO reactant mixture comprises hydrocarbons, oxygen, and optionally water; wherein the CPO reactor comprises a CPO catalyst; wherein the CPO reactor effluent comprises hydrogen ($H_2$), carbon monoxide (CO), carbon dioxide ($CO_2$), water, and unreacted hydrocarbons, wherein the CPO reactor effluent is characterized by a hydrogen to carbon monoxide ($H_2$/CO) molar ratio of the CPO reactor effluent, and wherein the CPO reactor effluent is characterized by an M ratio of the CPO reactor effluent, wherein the M ratio is a molar ratio defined as ($H_2-CO_2$)/(CO+$CO_2$);
    (b) feeding at least a portion of the CPO reactor effluent to water-gas shift (WGS) reactor to produce a hydrogen enriched reactor effluent, wherein a portion of the carbon monoxide of the CPO reactor effluent reacts with water via a WGS reaction to produce hydrogen and carbon dioxide, wherein the hydrogen enriched reactor effluent is characterized by a $H_2$/CO molar ratio of the hydrogen enriched reactor effluent, wherein the hydrogen enriched reactor effluent is characterized by an M ratio of the hydrogen enriched reactor effluent, and wherein the $H_2$/CO molar ratio of the hydrogen enriched reactor effluent is greater than the $H_2$/CO molar ratio of the CPO reactor effluent; and
    (c) removing a portion of the $CO_2$ from the hydrogen enriched reactor effluent in $CO_2$ separator to yield the syngas, wherein the syngas is characterized by an M ratio of the syngas, and wherein the M ratio of the syngas is greater than the M ratio of the CPO reactor effluent, and wherein the M ratio of the syngas is greater than the M ratio of the hydrogen enriched reactor effluent;
    wherein the process further comprises cooling the CPO reactor effluent and heating the hydrocarbons by: (i) exchanging heat between the CPO reactor effluent and a heat exchange fluid in a first heat exchanger to yield a first cooled CPO reactor effluent; (ii) heating the hydrocarbons while further cooling the first cooled CPO reactor effluent via heat exchange therebetween in a second heat exchanger to yield heated hydrocarbons and a second cooled CPO reactor effluent; and (iii) optionally heating the hydrocarbons prior to (ii) via an electrical heater, wherein the heated hydrocarbons comprise one or more sulfur-containing compounds, and wherein at least a portion of the sulfur-containing compounds is removed from the heated hydrocarbons to yield desulfurized hydrocarbons;
    wherein the process further comprises heating water while cooling the second cooled CPO reactor effluent by heat exchange in a third heat exchanger to yield a third cooled CPO reactor effluent, wherein at least a portion of the third cooled CPO reactor effluent is fed to the WGS reactor in step (b), and wherein at least a portion of a steam produced in the first heat exchanger and/or the third heat exchanger is used to power a steam-driven compressor.

2. The process of claim 1, wherein the hydrocarbons comprise methane, natural gas, natural gas liquids, associated gas, well head gas, enriched gas, paraffins, shale gas, shale liquids, fluid catalytic cracking (FCC) off gas, refinery process gases, naphtha gas, stack gases, fuel gas from a fuel gas header, or combinations thereof.

3. The process of claim 1, wherein the hydrocarbons further comprise one or more sulfur-containing compounds, and wherein at least a portion of the sulfur-containing compounds is removed from the hydrocarbons prior to introducing the hydrocarbons to the CPO reactor.

4. The process of any of claim 1, wherein the CPO reactor is characterized by at least one CPO operational parameter selected from the group consisting of a CPO inlet temperature of from about 200° C. to about 550° C.; a CPO outlet temperature of from about 600° C. to about 1,400° C.; a CPO pressure of from about 1 barg to about 90 barg; a CPO contact time of from about 0.001 milliseconds (ms) to about 5 seconds(s); a carbon to oxygen (C/O) molar ratio in the CPO reactant mixture of from about 1:1 to about 5:1, wherein the C/O molar ratio refers to the total moles of carbon (C) of hydrocarbons in the reactant mixture divided by the total moles of oxygen (O) in the reactant mixture; a steam to carbon (S/C) molar ratio in the CPO reactant mixture of from about 0 to about 3:1, wherein the S/C molar ratio refers to the total moles of water ($H_2O$) in the reactant mixture divided by the total moles of carbon (C) of hydrocarbons in the reactant mixture; and combinations thereof.

5. The process of claim 1, wherein the M ratio of the syngas is greater than or equal to about 1.7 and/or wherein less than about 50 mol % of the $C_{4+}$ in the hydrogen enriched reactor effluent is removed in the $C_{4+}$ separator to yield the syngas.

6. The process of claim 1, further comprising cooling the desulfurized hydrocarbons, wherein cooling the desulfurized hydrocarbons optionally comprises heating water while cooling the desulfurized hydrocarbons by heat exchange in a third heat exchanger to yield steam and cooled desulfurized hydrocarbons, wherein at least a portion of the cooled desulfurized hydrocarbons and optionally at least a portion of the steam are fed to the CPO reactor in step (a).

7. The process of claim 1, wherein at least a portion of the syngas is introduced to a compressor to yield compressed syngas, and further comprising (i) introducing at least a portion of the compressed syngas to a methanol synthesis loop to produce a crude methanol stream and a purge gas stream; wherein the crude methanol stream comprises methanol and water; and wherein the purge gas stream comprises hydrogen, carbon monoxide, carbon dioxide, and hydrocarbons.

8. The process of claim 7 further comprising:
introducing at least a portion of the purge gas stream, to a hydrogen separation unit to produce a hydrogen stream and a residual gas stream;
recycling at least a portion of the residual gas stream to the CPO reactor and/or utilizing at least a portion of the residual gas stream as fuel; and
recycling at least a portion of the hydrogen stream to the methanol synthesis loop and/or recycling at least a portion of the hydrogen stream to the CPO reactor.

* * * * *